United States Patent
Forthmann et al.

(10) Patent No.: US 8,379,791 B2
(45) Date of Patent: Feb. 19, 2013

(54) METHOD AND APPARATUS TO IMPROVE CT IMAGE ACQUISITION USING A DISPLACED GEOMETRY

(75) Inventors: Peter Forthmann, Sandesneben (DE); Thomas Koehler, Norderstedt (DE); Udo Van Stevendaal, Ahrensburg (DE); Matthias Bertram, Aachen (DE); Steffen Wiesner, Cologne (DE); Colas Schretter, Grez-Doiceau (BE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 13/120,660

(22) PCT Filed: Oct. 5, 2009

(86) PCT No.: PCT/IB2009/054353
§ 371 (c)(1), (2), (4) Date: Mar. 24, 2011

(87) PCT Pub. No.: WO2010/041193
PCT Pub. Date: Apr. 15, 2010

(65) Prior Publication Data
US 2011/0182400 A1 Jul. 28, 2011

Related U.S. Application Data

(60) Provisional application No. 61/104,358, filed on Oct. 10, 2008.

(51) Int. Cl.
*A61B 6/00* (2006.01)

(52) U.S. Cl. .................. 378/4; 378/8; 378/11; 378/20; 382/131

(58) Field of Classification Search ............... 378/4, 19
See application file for complete search history.

(56) References Cited

U.S. PATENT DOCUMENTS

| | | | | | |
|---|---|---|---|---|---|
| 4,200,799 | A | * | 4/1980 | Saito | 378/13 |
| 5,457,724 | A | * | 10/1995 | Toth | 378/4 |
| 5,768,331 | A | * | 6/1998 | Gordon et al. | 378/19 |
| 5,848,117 | A | * | 12/1998 | Urchuk et al. | 378/19 |
| 6,011,828 | A | * | 1/2000 | Hardy et al. | 378/65 |
| 6,118,841 | A | * | 9/2000 | Lai | 378/19 |
| 7,062,009 | B2 | * | 6/2006 | Karimi et al. | 378/19 |
| 2003/0123604 | A1 | * | 7/2003 | Edic et al. | 378/19 |
| 2004/0165695 | A1 | * | 8/2004 | Karimi et al. | 378/19 |
| 2006/0104407 | A1 | * | 5/2006 | Zamyatin et al. | 378/4 |
| 2007/0081624 | A1 | * | 4/2007 | Nabatame | 378/19 |
| 2008/0310584 | A1 | * | 12/2008 | Hey et al. | 378/15 |

* cited by examiner

*Primary Examiner* — Alexander H Taningco

(57) ABSTRACT

A method and apparatus are provided to improve CT image acquisition using a displaced acquisition geometry. A CT apparatus may be used having a source (102) and a detector (104) transversely displaced from a center (114) of a field of view (118) during acquisition of the projection data. The amount of transverse displacement may be determined based on the size of the object (108). The source and the detector may be adjusted to vary the size of the transverse field of view. The first data set acquired by the detector may be reconstructed and used to simulate missing projection data that could not be acquired by the detector at each projection angle. The measured projection data and the simulated projection data may be used to obtain a second data set. The second data set may be compared to the first data set to produce a corrected data set.

30 Claims, 6 Drawing Sheets

METHOD AND APPARATUS TO IMPROVE CT IMAGE ACQUISITION USING A DISPLACED GEOMETRY

CROSS REFERENCE TO RELATED APPLICATIONS

This application claims the benefit of U.S. provisional application Ser. No. 61/104,358 filed Oct. 10, 2008, which is incorporated herein by reference.

The present application relates to computed tomography ("CT"). In particular, it finds application in CT for medical applications.

It also finds application to article and security inspection, non-destructive testing, pre-clinical imaging, and other situations in which CT data can provide useful information about the structure or function of an object. One area in which CT imaging systems have gained widespread acceptance is in medicine, where CT scanners are widely used by radiologists and other medical professionals in connection with the diagnosis and treatment of disease.

U.S. patent application No. 60/822,678, filed on Aug. 17, 2006, which is incorporated herein by reference, describes a CT apparatus and method for acquiring projection data at a plurality of angular positions relative to an object disposed in an examination region. The CT apparatus includes an x-ray source and detector transversely displaced from a center of rotation in the transaxial plane (i.e., off-center, offset, or off-focus). A CT apparatus having offset geometry is desirable because it allows for an increased field of view. The x-ray source and detector rotate about the center of rotation and remain in a fixed mechanical relation to each other so as to acquire projection data at a plurality of projection angles. The x-ray source emits radiation having a transverse fan angle, and a complete angular sampling of a transverse field of view requires the acquisition of projection data over an angular range greater than 180 degrees plus the fan angle. The CT apparatus reconstructs the projection data generated by the CT apparatus using reconstruction techniques, such as filtered backprojection, to generate volumetric data indicative of the object under examination.

A CT apparatus having an offset x-ray source and detector may not completely illuminate the entire object under examination with the source in a single position. Further, filtering of the projection data during reconstruction involves a complete projection. Therefore, during reconstruction, the projection data acquired with the source in a single position may be extended using data acquired with the source in an opposing position in the transaxial plane. Due to the diverging rays of the cone-beam geometry, x-rays from the opposing cones do not complement each other outside the transaxial plane unless the shape of the object is constant and uniform in the axial direction. This divergence of the x-rays outside the transaxial plane causes errors during filtering. Further, larger x-ray source and detector offsets may deteriorate the quality of the reconstructed image. It is desirable to find an offset that permits a desired balance between the image quality and the size of the field of view for each object under examination.

Aspects of the present invention address these matters, and others.

According to one aspect of the present invention, a method and apparatus are provided to improve CT image acquisition using a displaced acquisition geometry.

In accordance with one aspect of the present invention, an apparatus is provided for acquiring tomographic projection data at a plurality of angular positions relative to an object disposed in an examination region. The apparatus includes a radiation source and a radiation sensitive detector which detects radiation emitted by the source. The source and a transverse center of the detector may be transversely displaced from a center of a transverse field of view during acquisition of the projection data. The amount of transverse displacement of the source and the transverse center of the detector from the center of the transverse field of view may be determined based on the size of the object. As such, an offset that permits a desired balance between the image quality and the size of the field of view may be determined.

According to another aspect, a computed tomography method is provided for acquiring tomographic projection data at a plurality of angular positions. A CT apparatus is used having a source and a transverse center of a detector transversely displaced from a center of a transverse field of view during acquisition of the projection data. The amount of transverse displacement of the source and detector may be determined based on the size of an object. As such, an offset that permits a desired balance between the image quality and the size of the field of view may be determined. The source and the detector may be adjusted to vary the size of the transverse field of view. Radiation may be emitted from the source at a first projection angle. The detector may acquire computed tomography projection data indicative of the first radiation at the first projection angle. This process may be repeated at each of a plurality of projection angles to acquire a CT data set.

According to another aspect, a method is provided for correcting tomographic projection data generated by a CT apparatus having a source and a transverse center of a detector transversely displaced from a center of a transverse field of view during acquisition of the projection data. Radiation is emitted from the source and the detector acquires computed tomography projection data at each of a plurality of projection angles to acquire a first CT data set. The first CT data set is reconstructed to generate volumetric data indicative of the object under examination. The volumetric data may be used to simulate missing projection data that could not be acquired by the detector at one or more projection angles. The simulated projection data may be used to obtain a second CT data set for at least one of the projection angles. The first CT data set is complemented with the second CT data set to produce a corrected CT data set. The corrected CT data set is reconstructed to generate corrected volumetric data indicative of the object.

Still further aspects of the present invention will be appreciated to those of ordinary skill in the art upon reading and understand the following detailed description.

Numerous additional advantages and benefits will become apparent to those of ordinary skill in the art upon reading the following detailed description of preferred embodiments. The invention may take form in various components and arrangements of components, and in various process operations and arrangements of process operations. The drawings are only for the purpose of illustrating preferred embodiments and are not to be construed as limiting the invention.

Figure 1:
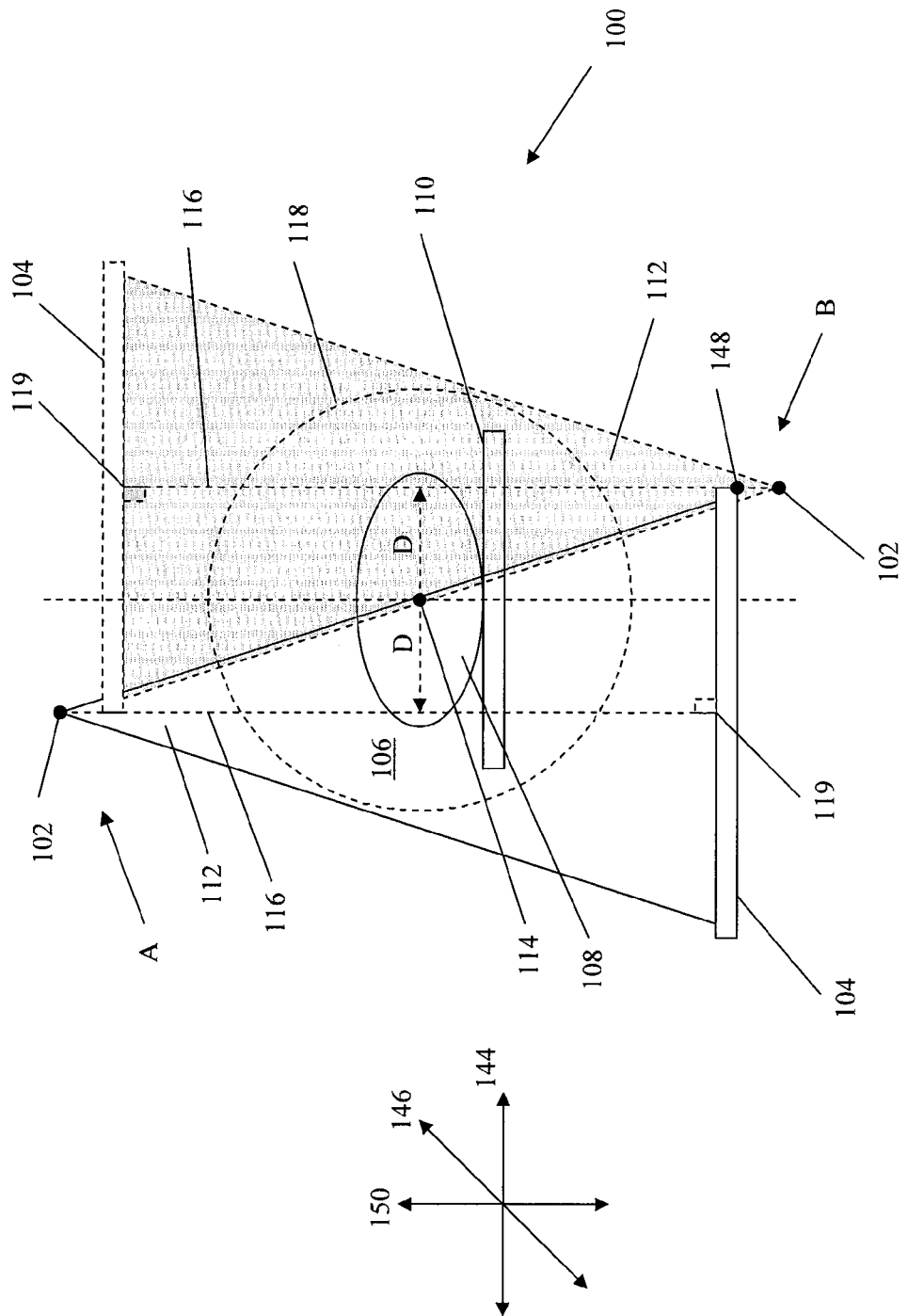
FIG. 1 is a transaxial view of a displaced CT acquisition geometry according to an embodiment of the invention.

The present application is directed generally to a method and apparatus for CT image acquisition using a displaced acquisition geometry. FIG. 1 depicts an exemplary CT apparatus geometry 100 having an x-ray source 102, such as an x-ray tube, and an x-ray sensitive detector 104, such as a flat panel area detector array extending in the transverse and axial directions, transversely displaced from a center of rotation 114 in the transaxial plane, or offset. As illustrated in FIG. 1, the center of rotation 114 may also serve as the center of the transverse field of view ("FOV") 118. However, those two axes are not necessarily so aligned in every application. As illustrated, an object support 110 supports the object under examination 108 in an examination region 106. A central ray or projection 116 of the x-ray beam 112 is perpendicular to the detector transverse center 119 but is displaced from the center of rotation 114.

While the figures and discussion are focused on the use of flat panel detectors, arcuate detectors may also be used. Further, while the figures and discussion focus on an x-ray CT system in which the source 102 is the focal spot of an x-ray tube and hence substantially a point source, other alternatives are contemplated. For example, the source 102 may be implemented as a line source. Wedge and other beam geometries are also contemplated. Gamma and other radiation sources may also be used. Multiple sources 102 and detectors 104 may also be provided, in which case corresponding sets of sources and detectors may be offset angularly and/or longitudinally from one another.

As illustrated in FIG. 1, the x-ray source 102 and the x-ray sensitive detector 104 rotate about the center of rotation 114. The source 102 and detector 104 are generally mounted to a rotating gantry (not shown) for rotation about the examination region 106. In some embodiments, however, the source 102 and detector 104 may remain at a constant angular position while the object 108 is moved and/or rotated to produce the requisite angular sampling.

As shown, the x-ray source 102 and detector 104 of the CT apparatus geometry 100 are depicted in two opposing positions in the transaxial plane. In position A, the central ray 116 of the x-ray beam 112 is offset a distance D from the center of rotation 114. In position B, the x-ray source 102 and detector 104 are rotated about the center of rotation 180 degrees from position A. However, the central ray 116 of the x-ray beam 112 (shown shaded) remains offset a distance D from the center of rotation 114.

For a detector 104 of given dimensions and the radial distance between the source 102 and the center of rotation 114, the size of the transverse FOV 118 can be varied by varying the distance D between the central ray 116 and the center of rotation 114. For example, full beam geometry corresponds to the situation where the central ray 116 intersects the center of rotation 114 (i.e., where D=0). The maximum FOV configuration corresponds to a situation in which the distance D is equal to one half the detector width. In this configuration, a rotation of approximately 360 degrees is needed to obtain a complete angular sampling, whereas a rotation of 180 degrees plus the fan or cone angle provides a complete angular sampling when configured in the full beam geometry. The requisite angular range for intermediate configurations varies between 180 degrees plus the fan angle and 360 degrees, and can readily be calculated from the geometry of the system 100.

As described in U.S. patent application No. 60/822,678, filed on Aug. 17, 2006, the distance D between the central ray 116 and the center of rotation 114 may be varied in multiple ways to vary the size of the transverse FOV 118. The source and detector may be shifted together or independently of each other (e.g., leaving the source in a central position and only shifting the detector). For example, the source 102 and detector 104 may be shifted in a direction 144 or 146 while keeping the center of rotation 114 unchanged. The source 102 and detector 104 may also be shifted in the direction 144, tangent to the transverse FOV 118, while the center of rotation 114 is displaced in a direction 150, which is perpendicular to the transverse FOV or to the major plane of the detector. Further, the detector 104 may be pivoted about a pivot axis 148 such that a ray of the x-ray beam 112 which intersects the transverse center 119 of the detector is perpendicular to the plane of the detector.

The source 102 and detector 104 may be shifted and/or pivoted to vary the size of the transverse FOV 118 by any suitable means. For example, the source 102 and detector 104 may be moved manually by a human user. The source 102 and detector 104 may be attached to adjustable sliders that allow the source and detector to move in various directions relative to the rotating gantry and the center of rotation 114. Further, the source 102 and detector 104 may be attached to a drive, such as a microstep motor, that provides the requisite motive force such that the source and detector may be moved and/or pivoted automatically.

The source 102 and detector 104 may be mounted to a common frame or otherwise so that the physical relationship between the source and detector is unchanged from one FOV configuration to another. However, in some embodiments, the source 102 and detector 104 may be shifted and/or pivoted separately from one FOV configuration to another. The system may have to be calibrated for the various source 102 and detector 104 positions, potentially requiring separate blank or calibrations scans.

As stated, it is desirable to find an offset that permits a desired balance, or trade-off, between the image quality and the size of the field of view. Larger offsets increase the field of view but may deteriorate the quality of the reconstructed image. On the other hand, smaller offsets decrease the field of view but may improve the quality of the reconstructed image. Often, the optimal offset will be the minimal offset necessary to maintain the object within the FOV. A scanning configuration that includes the smallest x-ray source 102 and detector 104 offset for the object under examination while maintaining the object within the FOV 118 may be determined in a variety of ways. For example, if the size and shape of the object under examination is known or estimated, the minimum size of the FOV 118 needed to accommodate the object can be determined. The distance D between the central ray 116 and the center of rotation 114 may be varied, as described above, to produce a FOV 118 having the minimum size. Further, the minimum x-ray source 102 and detector 104 offset may be determined directly.

The size and shape of the object under examination may be determined using a variety of methods. For example, the size and shape of the object may be determined from the results of an initial scan of the object. The results from a three dimensional low-dose scout scan having a large offset (e.g., a free breathing acquisition for attenuation correction) may be used. The results from a low dose planar x-ray image at maximum offset may also be used. If the object under examination is a human, a pair of Anterior-Posterior (AP) and Posterior-Anterior (PA) views may be sufficient because a human body is generally an elliptical shape. Further, the size and shape of the object may be determined using the results from an initial single photon emission CT ("SPECT") scan, positron emission tomography ("PET") scan, or a magnetic resonance image ("MRI"). The size and shape of the object may also be determined by manual measurement of the object's extent (e.g., height, width, girth, etc.).

The minimum x-ray source 102 and detector 104 offset may be determined directly using an optical means, such as a laser attached to the rotating gantry with photodiodes attached to the detector. The laser might be mounted with or near the x-ray source 102. For example, the laser may be moved, or pivoted, across or rotated around the object under examination. The object being imaged and perhaps the associated object support will prevent the light beam emitted from the laser from reaching the photodiodes. When the laser beam moves beyond the extent of the object, the photodiodes will detect the light beam and the extent of the object may be measured. Therefore, the minimum FOV 118 and offset can be determined. This process may be automated by any suitable means, such as for example, the laser and/or detector may be moved or pivoted across or rotated around the object with use of a motor.

As discussed, the source 102 and detector 104 may be attached to a drive, such as a microstep motor, that provides the requisite motive force such that the source and detector may be moved and/or pivoted automatically. Therefore, as the scan proceeds and the gantry rotates, the offset or angle of the source 102 and detector 104 may be changed for each projection. Further, the offset or angle of the source 102 and detector 104 may be changed at different positions along the longitudinal axis 416. Using the minimum FOV 118 and offset information generated by the methods described above or the like, the offset or angle of the source 102 and detector 104 may be changed accordingly for each projection or along the longitudinal axis by the drive.

Figure 2:
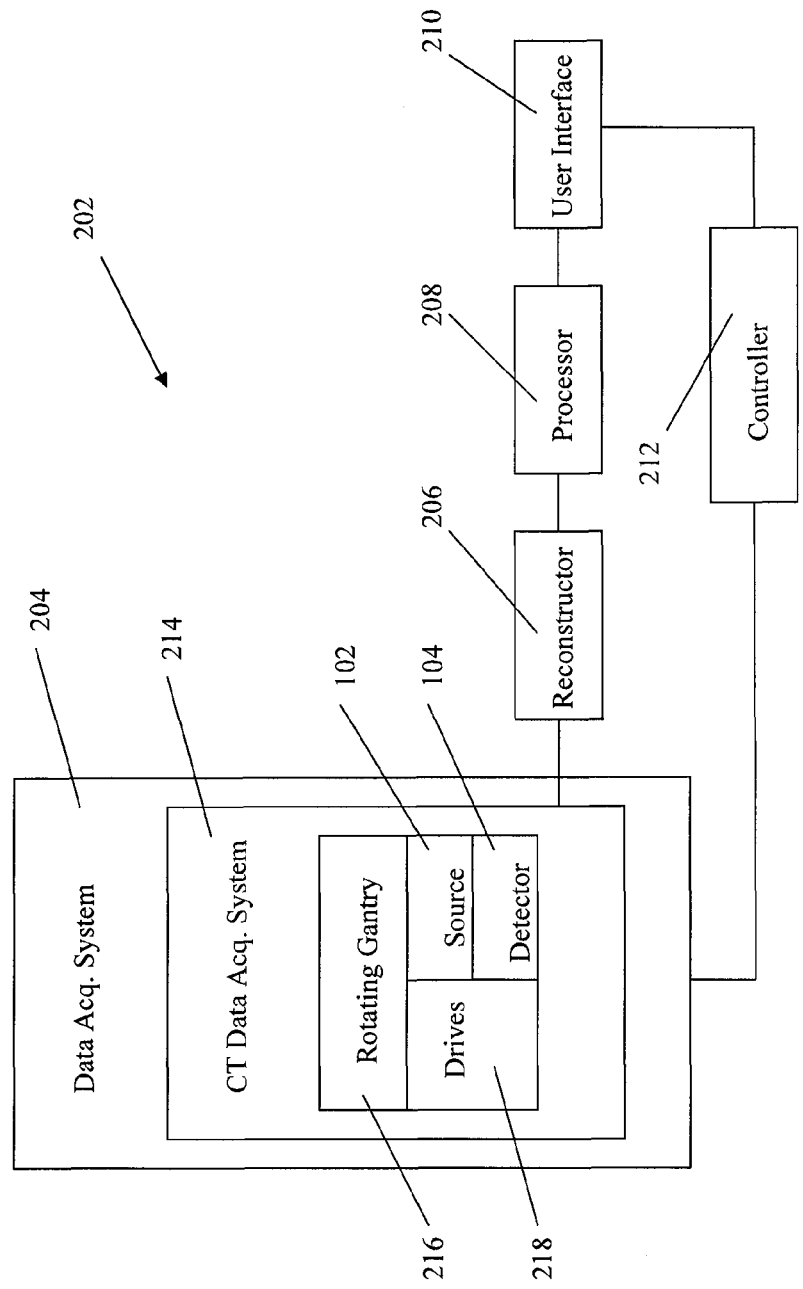
FIG. 2 depicts an imaging system according to an embodiment of the invention.

FIG. 2 depicts an imaging system 202 suitable for use with the exemplary CT apparatus geometry 100. The system 202 includes a data acquisition system 204, a reconstructor 206, image processor 208, a user interface 210, and a controller 212.

The data acquisition system 204 includes a CT data acquisition system 214 in which the source 102 and detector 104 are mounted to a rotating gantry 216 for rotation about the examination region. Circular, 360 degrees or other angular sampling ranges as well as axial, helical, circle and line, saddle, or other desired scanning trajectories may be implemented, for example by moving the object support 110 longitudinally in coordination with rotation of the rotating gantry 216.

In one implementation, the source 102 and detector 104 are fixedly mounted in relation to the rotating gantry 216 so that the acquisition geometry is fixed. In another, the source 102 and detector 104 are movably mounted to the rotating gantry 216 so that the acquisition geometry is variable, for example to allow the relative movement described above. In such an implementation, one or more drives 218 may provide the requisite motive force. Alternately, the source 102 and detector 104 may be moved manually by a human user.

A reconstructor 206 reconstructs the data generated by the data acquisition system 204 using reconstruction techniques to generate volumetric data indicative of the object under examination. Reconstruction techniques include analytical techniques such as filtered backprojection, as well as iterative techniques. Further inventive reconstruction techniques are described below with reference to FIG. 4.

An image processor 208 processes the volumetric data as required, for example for display in a desired fashion on a user interface 210, which may include one or more output devices such as a monitor and printer and one or more input devices such as a keyboard and mouse.

The user interface 210, which is advantageously implemented using software instructions executed by a general purpose or other computer so as to provide a graphical user interface ("GUI"), allows the user to control or otherwise interact with the imaging system 202, for example by selecting a desired FOV configuration or dimension, initiating and/or terminating scans, selecting desired scan or reconstruction protocols, manipulating the volumetric data, and the like. In one implementation, one or both of the FOV configuration and reconstruction protocol are established automatically by the imaging system 202 based on a scan protocol selected by the user. As yet another example, the user interface 210 may prompt or otherwise allow the user to enter a desired transverse radius, diameter or other FOV dimension. In such an implementation, the information from the user is used to automatically calculate the requisite position(s) of the source 102 and/or detector 104.

A controller 212 operatively connected to the user interface 210 controls the operation of the data acquisition system 204, for example to carry out a desired scan protocol, cause the drive(s) 218 to position the source 102 and/or detector 104 so as to provide the desired FOV, and the like.

The aforementioned functions, such as for example, selecting a desired FOV configuration or dimension, initiating and/or terminating scans, selecting desired scan or reconstruction protocols, manipulating the volumetric data, and the like, can be performed as software logic. "Logic," as used herein, includes but is not limited to hardware, firmware, software and/or combinations of each to perform a function(s) or an action(s), and/or to cause a function or action from another component. For example, based on a desired application or needs, logic may include a software controlled microprocessor, discrete logic such as an application specific integrated circuit (ASIC), or other programmed logic device. Logic may also be fully embodied as software.

"Software," as used herein, includes but is not limited to one or more computer readable and/or executable instructions that cause a computer or other electronic device to perform functions, actions, and/or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, and/or the desires of a designer/programmer or the like.

The systems and methods described herein can be implemented on a variety of platforms including, for example, networked control systems and stand-alone control systems. Additionally, the logic, databases or tables shown and described herein preferably reside in or on a computer readable medium, such as a component of the imaging system 202. Examples of different computer readable media include Flash Memory, Read-Only Memory (ROM), Random-Access Memory (RAM), programmable read-only memory (PROM), electrically programmable read-only memory (EPROM), electrically erasable programmable read-only memory (EEPROM), magnetic disk or tape, optically readable mediums including CD-ROM and DVD-ROM, and others. Still further, the processes and logic described herein can be merged into one large process flow or divided into many sub-process flows. The order in which the process flows herein have been described is not critical and can be rearranged while still accomplishing the same results. Indeed, the process flows described herein may be rearranged, consolidated, and/or re-organized in their implementation as warranted or desired.

Figure 3:
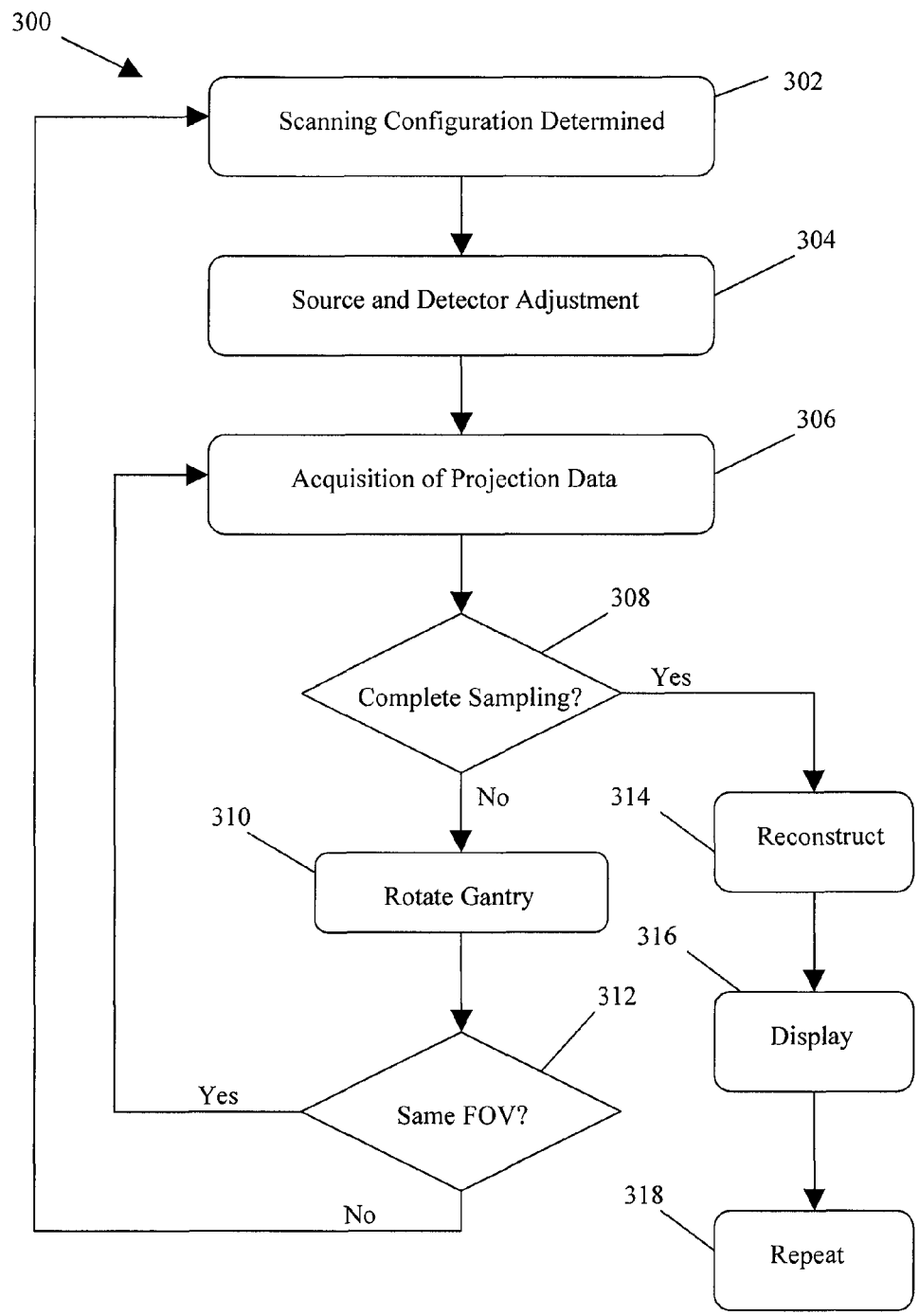
FIG. 3 depicts an imaging method according to an embodiment of the invention.

For example, such a process 300 is shown in FIG. 3. Initially, as shown in FIG. 3, a scanning configuration is determined for an initial angular position at step 302. The scanning configuration includes the smallest x-ray source 102 and detector 104 offset for the object under examination while maintaining the object within the FOV 118. The minimal offset may be determined using the data generated by any of the methods described above or other methods. The minimal offset may also vary between the scans taken at various angular positions about the examination region 106 and along the longitudinal axis. The positions of the source 102 and detector 104 are adjusted at step 304 to provide the desired FOV configuration at a current angular position. A scan is taken at step 306 so as to acquire projection data at the current angular position.

Whether the current angular position of step 306 is the last of a plurality of angular positions about the examination region 106 needed to obtain a complete angular sampling is determined at step 308. The angular range needed to sample the transverse FOV 118 is again a function of the system geometry. If the current angular position of step 306 is the last, then the scan data is reconstructed at step 314 and displayed in a desired format at step 316. If not, then the gantry 216 is rotated to the next angular position at step 310.

Whether the FOV configuration at the next angular position of step 310 is the same as the last FOV configuration is determined at step 312. If so, a scan is taken at step 306 so as to acquire projection data at the next angular position. If the FOV configuration is different, however, a scanning configuration is determined for the next angular position at step 302. The positions of the source 102 and detector 104 are adjusted at step 304 to provide the desired FOV configuration at the next angular position. A scan is taken at step 306 so as to acquire projection data at the next angular position.

At step 318, the process is repeated as desired, for example to scan a succession of patients. Note that additional scan(s) may be obtained prior to reconstructing and/or displaying the data acquired in given scan.

Figure 4:
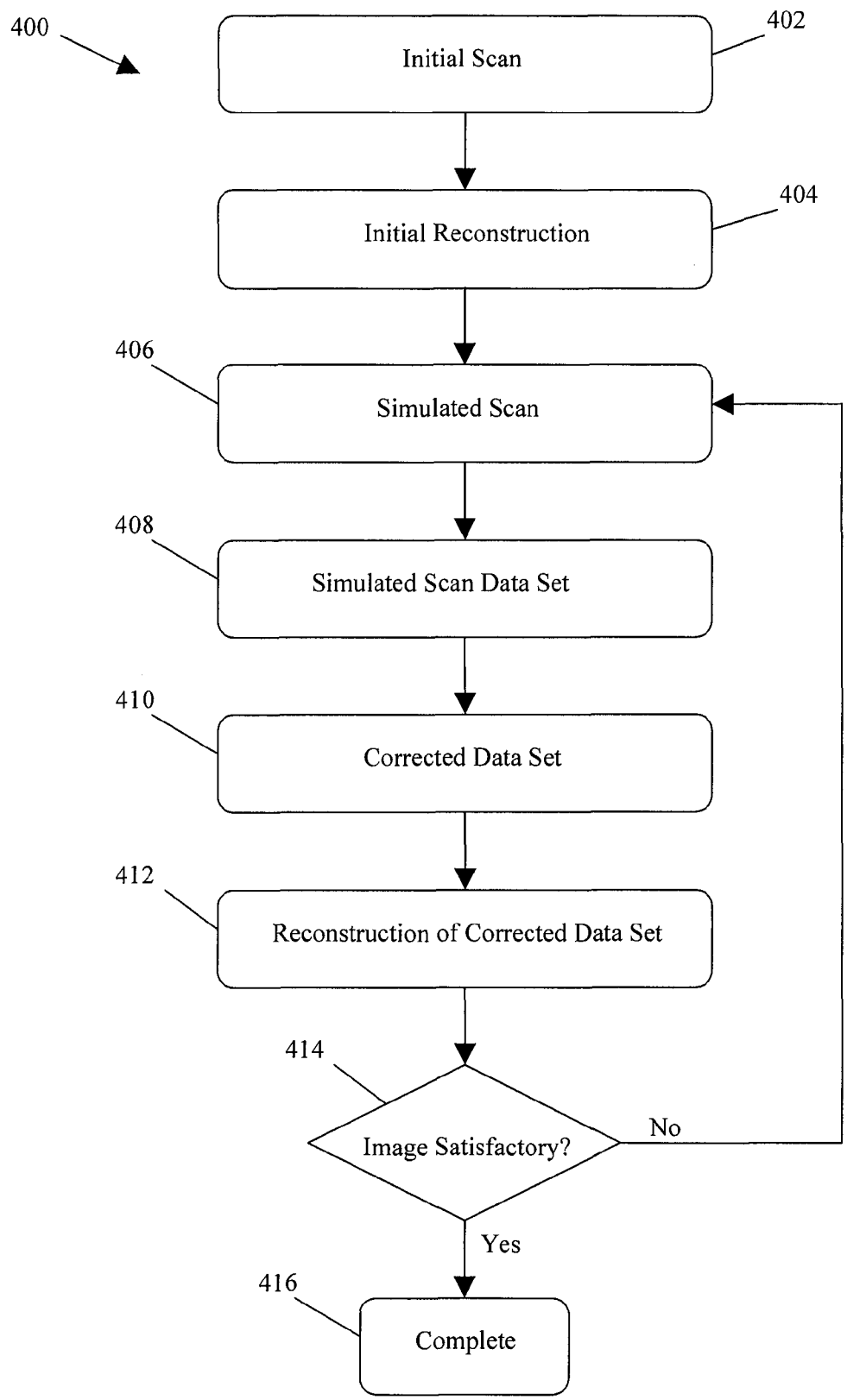
FIG. 4 depicts an image reconstruction method according to an embodiment of the invention.

An exemplary process 400 of reconstructing scan data is shown in FIG. 4. Initially, as shown in FIG. 4, an initial scan, or first pass, is acquired at step 402. Projection data from a plurality of angular positions about the examination region 106 is used in step 402 to obtain a complete angular sampling data set (i.e., measured data).

The reconstructor 206 reconstructs the projection data set of step 402 using reconstruction techniques to generate volumetric data indicative of the object under examination 108 at step 404. Initial reconstruction techniques include analytical techniques such as filtered backprojection, as well as iterative techniques. As stated, a CT apparatus having an offset x-ray source 102 and detector 104 may not completely illuminate the entire object under examination 108 with the source in a single position. Further, filtering of the projection data during reconstruction involves a complete projection. Therefore, during reconstruction in step 404, the projection data acquired with the source 102 in a single position (e.g., position A in FIG. 1) may be extended using data acquired with the source in an opposing position (e.g., position B in FIG. 1) in the transaxial plane. Due to the diverging rays of the cone-beam geometry, x-rays from the opposing cones do not complement each other outside the transaxial plane unless the shape of the object is constant and uniform in the axial direction. This divergence of the x-rays outside the transaxial plane causes errors during filtering.

Figure 5A:
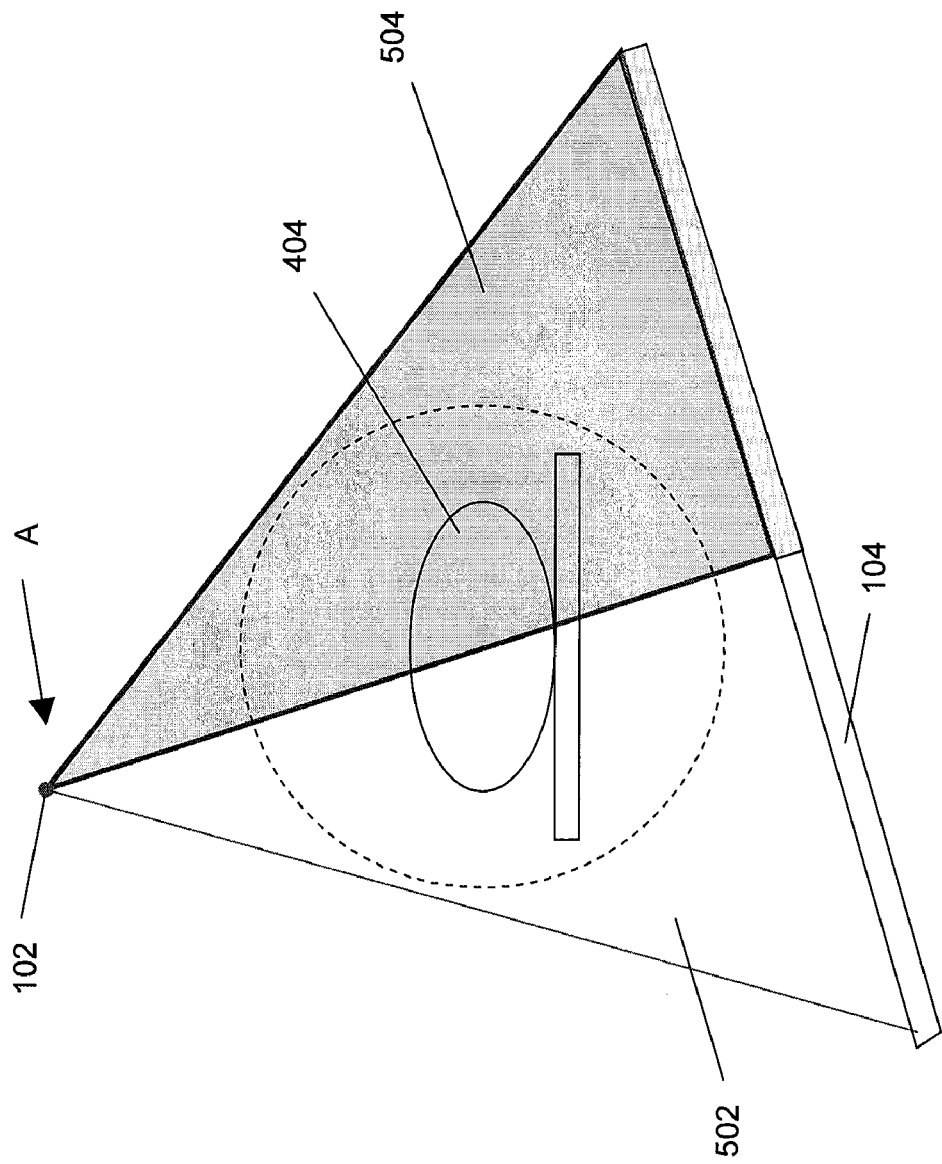
FIGS. 5A and 5B are transaxial views depicting projection data of a simulated scan of the image reconstruction method of FIG. 4.
Figure 5B:
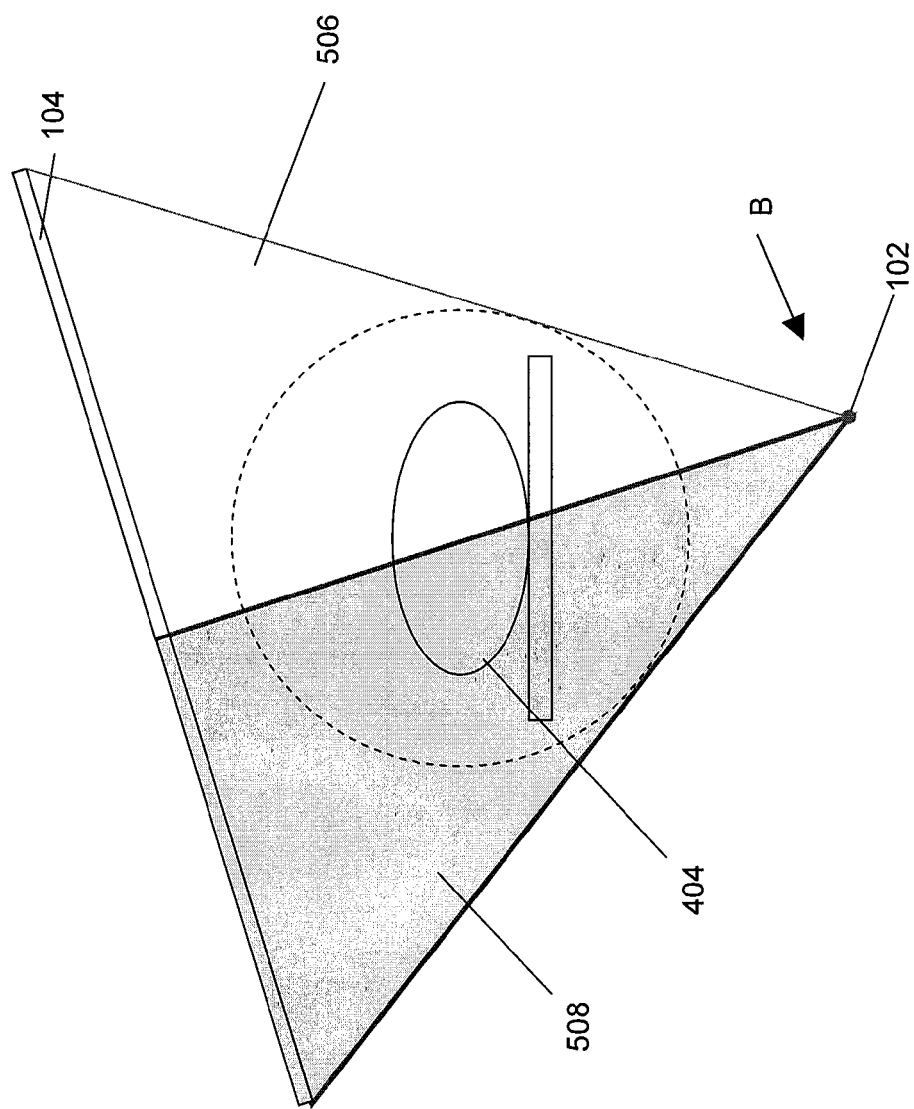

To improve the quality of the filtering step, a simulated scan, or second pass, is completed at step 406 using the reconstructed image of step 404 to simulate the missing projection data for each angular position that could not be acquired with the offset source 102 and detector 104. The data from the simulated scan is rebinned to a normal flat detector. For example, a simulated scan taken with the source 102 and detector 104 in position A is shown in FIG. 5A. As shown, the measured projection data 502 from the initial scan of step 402 is extended using simulated projection data 504 from the initial reconstruction of step 404. Similarly, FIG. 5B shows a simulated scan taken with the source 102 and detector 104 in position B. In FIG. 5B, the measured projection data 506 from the initial scan of step 402 is extended using simulated projection data 508 from the initial reconstruction of step 404.

At step 408, the projection data of the simulated scan of step 406 from a plurality of angular positions about the examination region 106 is used to obtain a complete angular sampling data set (i.e., simulated data). The projection data of the simulated data set is complete, which permits filtering of the projection data during reconstruction. At step 410, the initial scan data set, or measured data, of step 402 is complemented with the simulated projection data, or simulated data, of step 408 to produce a corrected data set that is more indicative of the object under examination. For example, the simulated data may be added to the measured data. Further, smooth weighting, or some other form of processing, may occur in the overlap region to permit a smooth transition from the measured data to the simulated data. At step 412, the corrected data set is reconstructed using the reconstruction techniques described above in step 404 to generate volumetric data indicative of the object under examination.

Whether the image generated from the reconstruction of the corrected data set in step 412 contains errors or is unsatisfactory is determined at step 414. If the image contains errors or is unsatisfactory, a second simulated scan, or third pass, may be completed at step 406 using the reconstructed image of step 412 to simulate the missing projection data for each angular position that could not be acquired with the offset source 102 and detector 104. This process may be completed multiple times until the quality of the image is satisfactory. If the image generated from the reconstruction of the corrected data set in step 412 is satisfactory, the reconstruction is complete at step 416.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. An apparatus for acquiring tomographic projection data at a plurality of angular positions relative to an object disposed in an examination region, the apparatus comprising:
   a rotating gantry which rotates around a central axis of rotation, wherein the examination region lies within the rotating gantry and includes a transaxial plane which is perpendicular to the central axis of rotation;
   a radiation source mounted on the rotating gantry for rotation about the examination region;
   a radiation sensitive detector mounted on the rotating gantry for rotation about the examination region to detect radiation emitted by the source, wherein the radiation has traversed the examination region;

wherein at least one of the source and a transverse center of the detector is transversely displaced from a center of a transverse field of view in the transaxial plane during acquisition of the projection data by a variable amount of displacement; and wherein the variable amount of transverse displacement is determined at least in part based on a size of the object in the transverse field of view.

2. The apparatus of claim 1, wherein the source and the transverse center of the detector are moved relative to the center of the transverse field of view to vary the size of the transverse field of view.

3. The apparatus of claim 2, wherein the source and detector are moved manually by a human user.

4. The apparatus of claim 2, wherein the source and detector are moved automatically by a drive.

5. The apparatus of claim 2, wherein the source and detector are moved together such that the physical relationship between the source and detector is unchanged.

6. The apparatus of claim 2, wherein the source and detector are moved separately.

7. The apparatus of claim 1, wherein the amount of transverse displacement varies between angular positions relative to the object disposed in the examination region.

8. The apparatus of claim 1, wherein the amount of transverse displacement varies along the central axis of the apparatus.

9. The apparatus of claim 1, wherein the amount of transverse displacement is determined to minimize a transverse field of view while still maintaining the object within the transverse field of view.

10. The apparatus of claim 1, wherein the size of the object is determined using an initial scan of the object.

11. The apparatus of claim 10, wherein the initial scan comprises a three dimensional low-dose scout scan.

12. The apparatus of claim 10, wherein the initial scan comprises obtaining a low-dose planar x-ray image.

13. The apparatus of claim 10, wherein the initial scan comprises at least one of a single photon emission computed tomography scan, a positron emission tomography scan, and a magnetic resonance scan.

14. The apparatus of claim 1, wherein the size of the object is determined using manual measurements of the object.

15. The apparatus of claim 1 further comprising a reconstructor that reconstructs a first CT data set acquired by the detector to generate first volumetric data indicative of the object, uses the first volumetric data to simulate missing projection data that could not be acquired by the detector at each angular position, uses the simulated projection data to obtain a second CT data set for at least one of the plurality of angular positions, complements the first CT data set with the second CT data set to produce an initial corrected CT data set, and reconstructs the initial corrected CT data set to generate corrected volumetric data indicative of the object.

16. An apparatus for acquiring tomographic projection data at a plurality of angular positions relative to an object disposed in an examination region, the apparatus comprising:
a radiation source;
a radiation sensitive detector which detects radiation emitted by the source, wherein the radiation has traversed the examination region;
wherein at least one of the source and a transverse center of the detector is transversely displaced from a center of a transverse field of view during acquisition of the projection data by a variable amount of displacement;
wherein the variable amount of transverse displacement is determined at least in part based on a size of the object in the transverse field of view; and
wherein the amount of transverse displacement is determined using a light source attached to a rotating gantry and a light detector attached to the radiation sensitive detector.

17. A computed tomography method, comprising the steps of:
acquiring tomographic projection data at a plurality of angular positions relative to an object disposed in an examination region, using a radiation source and a radiation sensitive detector to detect radiation emitted by the source, wherein the source and the detector are mounted on a rotating gantry which rotates around a central axis of rotation, and the examination region lies within the rotating gantry and includes a transaxial plane which is perpendicular to the central axis of rotation, and at least one of the source and a transverse center of the detector are transversely displaced from a center of a transverse field of view in the transaxial plane during acquisition of the projection data by a variable amount of displacement;
determining the variable amount of transverse displacement based at least in part on a size of an imaged object in the transverse field of view;
adjusting at least one of the source and the transverse center of the detector to correspond to the amount of determined transverse displacement; and
using the acquired tomographic projection data to generate a CT image of the imaged object.

18. The method of claim 17 further comprising repeating the steps of determining the amount of transverse displacement based on the size of the object and adjusting at least one of the source and the detector to correspond to the determined transverse displacement at each one of the plurality of angular positions to acquire a first CT data set.

19. The method of claim 17, further comprising reconstructing a first CT data set acquired by the detector to generate first volumetric data indicative of the object, using the first volumetric data to simulate missing projection data that could not be acquired by the detector at each angular position, using the simulated projection data to obtain a second CT data set for at least one of the plurality of angular positions, complementing the first CT data set with the second CT data set to produce an initial corrected CT data set, and reconstructing the initial corrected CT data set to generate corrected volumetric data indicative of the object.

20. The method of claim 17, wherein the amount of transverse displacement varies between angular positions relative to the imaged object.

21. The method of claim 17, wherein the amount of transverse displacement varies along the central axis.

22. The method of claim 17, wherein the amount of transverse displacement is determined to minimize the transverse field of view while still maintaining the object within the transverse field of view.

23. The method of claim 17, wherein the size of the object is determined using an initial scan of the object.

24. The method of claim 17, wherein the size of the object is determined using manual measurements of the object.

25. A computed tomography method, comprising the steps of:
acquiring tomographic projection data at a plurality of angular positions relative to an object disposed in an examination region, using a radiation source and a radiation sensitive detector to detect radiation emitted by the source, wherein at least one of the source and a transverse center of the detector are transversely displaced from a center of a transverse field of view during acquisition of the projection data by a variable amount of displacement;

determining the variable amount of transverse displacement based at least in part on a size of an imaged object in the transverse field of view;

adjusting at least one of the source and the transverse center of the detector to correspond to the amount of determined transverse displacement;

using the acquired tomographic projection data to generate a CT image of the imaged object; and wherein the amount of transverse displacement is determined using a light source attached to a rotating gantry and a light detector attached to the radiation sensitive detector.

26. A computed tomography method, comprising the steps of:

acquiring tomographic projection data at a plurality of angular positions relative to an object disposed in an examination region to acquire a first CT data set, using a radiation source and a radiation sensitive detector to detect radiation emitted by the source, wherein the source and the detector are mounted on a rotating gantry which rotates around a central axis of rotation, and the examination region lies within the rotating gantry and includes a transaxial plane which is perpendicular to the central axis of rotation, and at least one of the source and a transverse center of the detector are transversely displaced from a center of a transverse field of view in the transaxial plane during acquisition of the projection data by a variable amount of displacement, as determined at least in part based on a size of the object in the transverse field of view;

reconstructing the first CT data set to generate first volumetric data indicative of the object;

using the first volumetric data to simulate missing projection data that could not be acquired by the detector at each angular position;

using the simulated projection data to obtain a second CT data set for at least one of the plurality of angular positions;

complementing the first CT data set with the second CT data set to produce an initial corrected CT data set; and reconstructing the initial corrected CT data set to generate first corrected volumetric data indicative of the object.

27. The method of claim 26 further comprising the steps of:

using the first corrected volumetric data to simulate missing projection data that could not be acquired by the detector at each angular position;

using the simulated projection data from the first corrected volumetric data to obtain a third CT data set for at least one of the plurality of angular positions;

complementing the first CT data set with the third CT data set to produce a second corrected CT data set; and reconstructing the second corrected CT data set to generate second corrected volumetric data indicative of the object.

28. A computed tomography method, comprising the steps of:

acquiring tomographic projection data at a plurality of angular positions relative to an object disposed in an examination region to acquire a first CT data set, using a radiation source and a radiation sensitive detector to detect radiation emitted by the source, wherein the source and the detector are mounted on a rotating gantry which rotates around a central axis of rotation, and the examination region lies within the rotating gantry and includes a transaxial plane which is perpendicular to the central axis of rotation, and a transverse center of the detector is transversely displaced from a center of a transverse field of view in the transaxial plane during acquisition of the projection data by a variable amount of displacement, as determined at least in part based on a size of the object in the transverse field of view;

reconstructing the first CT data set acquired by the transversely displaced detector to generate first volumetric data indicative of the object;

using the first volumetric data to simulate missing projection data that could not be acquired by the transversely displaced detector at each angular position, wherein the simulated data set is rebinned to a flat detector having a transverse center substantially aligned with the center of the transverse field of view;

extending the first CT data set acquired by the transversely displaced detector using the simulated projection data to obtain a second CT data set for at least one of the plurality of angular positions;

complementing the first CT data set acquired by the transversely displaced detector with the second CT data set to produce an initial corrected CT data set; and reconstructing the initial corrected CT data set to generate first corrected volumetric data indicative of the object.

29. An apparatus for acquiring tomographic projection data at a plurality of angular positions relative to an object disposed in an examination region, the apparatus comprising:

a rotating gantry which rotates around a central axis of rotation, wherein the examination region lies within the rotating gantry and includes a transaxial plane which is perpendicular to the central axis of rotation;

a radiation source mounted on the rotating gantry for rotation about the examination region;

a radiation sensitive detector mounted on the rotating gantry for rotation about the examination region to detect radiation emitted by the source, wherein the radiation has traversed the examination region;

wherein at least one of the source and a transverse center of the detector is transversely displaced from a center of a transverse field of view during acquisition of the projection data by a variable amount of displacement, as determined at least in part based on a size of the object in the transverse field of view; and a reconstructor that:

reconstructs a first CT data set acquired by the detector to generate first volumetric data indicative of the object;

uses the first volumetric data to simulate missing projection data that could not be acquired by the detector at each projection angle;

uses the simulated projection data to obtain a second CT data set for at least one of the plurality of projection angles;

complements the first CT data set with the second CT data set to produce an initial corrected CT data set; and reconstructs the initial corrected CT data set to generate first corrected volumetric data indicative of the object.

30. The apparatus of claim 29 further comprising an image processor that processes the corrected volumetric data for display on a user interface.

* * * * *